US00PP16223P2

(12) United States Plant Patent
Mallet

(10) Patent No.: US PP16,223 P2
(45) Date of Patent: Jan. 31, 2006

(54) ***HYDRANGEA* PLANT NAMED 'SHAMROCK'**

(50) Latin Name: *Hydrangea macrophylla*
Varietal Denomination: Shamrock

(75) Inventor: Corinne Mallet, Varengeville sur Mer (FR)

(73) Assignee: Spring Meadow Nursery, Inc., Grand Haven, MI (US)

( * ) Notice: Subject to any disclaimer, the term of this patent is extended or adjusted under 35 U.S.C. 154(b) by 101 days.

(21) Appl. No.: 10/968,807

(22) Filed: Oct. 19, 2004

(51) Int. Cl.
*A01H 5/00* (2006.01)

(52) U.S. Cl. ..... Plt./250
(58) Field of Classification Search ..... Plt./250
See application file for complete search history.

(56) References Cited

U.S. PATENT DOCUMENTS

PP15,175 P3 * 9/2004 Dirr ..... Plt./250
2004/0064864 P1 * 4/2004 Dirr ..... Plt./250

OTHER PUBLICATIONS http://www.djroger.com/shamrock_hydrangea.htm.*
http://www.tangledroots.biz/plants/shamrock.htm.*
http://www.pottedliners.com/shamrock.htm.*
UPOV ROM GTITM Computer Database, GTI Jouve Retrieval Software 2004/06 Citation(s) for 'Shamrock'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Hydrangea* plant named 'Shamrock', characterized by its upright and outwardly spreading plant habit; lacecap-type inflorescences; double-type sterile flowers; and pink-colored flowers that become closer to dark red in color with development.

1 Drawing Sheet

Botanical designation: *Hydrangea macrophylla.*
Variety denomination: 'Shamrock'.

BACKGROUND OF THE INVENTION

The present Invention relates to a new and distinct cultivar of *Hydrangea* plant, botanically known as *Hydrangea macrophylla*, and hereinafter referred to by the cultivar name Shamrock.

The new *Hydrangea* originated from an open-pollination in 1998 of a unnamed selection of *Hydrangea macrophylla*, not patented, as the female, or seed, parent with an unknown selection of *Hydrangea macrophylla*, not patented, as the male, or pollen, parent. The cultivar Shamrock was discovered and selected by the Inventor as a single plant within the progeny of the stated open-pollination in a controlled environment in Varengeville Sur Mer, France.

Asexual reproduction of the new cultivar by softwood cuttings taken in Varengeville Sur Mer, France since the spring of 2000, has shown that the unique features of this new *Hydrangea* are stable and reproduced true to type in successive generations.

SUMMARY OF THE INVENTION

Plants of the cultivar Shamrock have not been observed under all possible environmental conditions. The phenotype may vary somewhat with variations in environment such as temperature and light intensity without, however, any variance in genotype.

The following traits have been repeatedly observed and are determined to be the unique characteristics of 'Shamrock'. These characteristics in combination distinguish 'Shamrock' as a new and distinct cultivar:

1. Upright and outwardly spreading plant habit.
2. Lacecap-type inflorescences.

3. Double-type sterile flowers.
4. Pink-colored flowers that become closer to dark red in color with development.

Plants of the new *Hydrangea* differ from plants of female parent in flower form as plants of the female parent selection do not have double-type sterile flowers.

Plants of the new *Hydrangea* can be compared to plants of the *Hydrangea macrophylla* cultivar Izu-No-Hana, not patented. In side-by-side comparisons conducted in Grand Haven, Mich., plants of the new *Hydrangea* differed from plants of the cultivar Izu-No-Hana in the following characteristics:

1. Plants of the new *Hydrangea* were more compact than plants of the cultivar Izu-No-Hana.
2. Plants of the new *Hydrangea* had smaller leaves than plants of the cultivar Izu-No-Hana.
3. Flower buds of plants of the new *Hydrangea* were hardier than flowers buds of plants of the cultivar Izu-No-Hana.
4. Plants of the new *Hydrangea* had larger sterile flowers than plants of the cultivar Izu-No-Hana.
5. Plants of the new *Hydrangea* and the cultivar Izu-No-Hana differed in flower coloration.

BRIEF DESCRIPTION OF THE PHOTOGRAPHS

The accompanying colored photographs illustrate the unique appearance of the new cultivar, showing the colors as true as it is reasonably possible to obtain in colored reproductions of this type. Colors in the photographs may differ from the color values cited in the detailed botanical description which accurately describe the colors of the new *Hydrangea.*

The photograph at the bottom of the first sheet is a side perspective view of a typical plant of 'Shamrock'.

The photograph at the top of the sheet comprises a close-up view of a typical inflorescence of 'Shamrock'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and in the following description were grown in Grand Haven, Mich., in ground beds in an outdoor nursery and under conditions which closely approximate commercial production conditions. During the production of the plants, day temperatures ranged from 20 to 30° C. and night temperatures ranged from 12 to 20° C. Plants were about four years old when the photographs and description were taken. Photographs and description were taken during the summer.

Botanical classification: *Hydrangea macrophylla* cultivar Shamrock.

Parentage:

*Female, or seed, parent.*—Unnamed selection of *Hydrangea macrophylla*, not patented.

*Male, or pollen, parent.*—Unknown *Hydrangea macrophylla* selection, not patented.

Propagation:

*Type cutting.*—By softwood cuttings.

*Time to initiate roots.*—About ten days at 23° C.

*Time to produce a rooted cutting or liner.*—About two months at 23° C.

*Root description.*—Fine, fibrous; creamy white in color.

*Rooting habit.*—Freely branching; dense.

Plant description:

*Form/growth habit.*—Upright and outwardly spreading plant habit; round in overall shape; dense and bushy perennial shrub. Vigorous growth habit.

*Plant height, soil level to top of plant plane.*—About 60 cm.

*Plant diameter or area of spread.*—About 50 cm.

*Branching habit.*—Freely branching, about 24 lateral branches per plant. Pruning will enhance branching potential.

*Lateral branches.*—Length: About 60 cm. Diameter: About 1 cm. Internode length: About 7 cm. Texture: Smooth, glabrous. Color: 145A.

*Foliage description.*—Arrangement: Opposite, simple. Length: About 20 cm. Width: About 8.5 cm. Shape: Ovate. Apex: Acute. Base: Attenuate. Margin: Crenate to serrate. Texture, upper and lower surfaces: Smooth, glabrous. Venation pattern: Pinnate. Color: Developing and fully expanded foliage, upper surface: 146A. Developing and fully expanded foliage, lower surface: 144A. Venation, upper surface: 146A. Venation, lower surface: 144A. Petiole: Length: About 2 cm. Diameter: About 4 mm. Texture, upper and lower surfaces: Smooth, glabrous. Color, upper and lower surfaces: 144A.

Flower description:

*Flower type and habit.*—Single fertile and sterile flowers arranged on flattened terminal clusters in a lacecap formation. Sterile flowers with large showy sepals without petals and reproductive organs. Fertile flowers small with petals, sepals and reproductive organs. Flowers face upward and outwardly. Flowers persistent. Flowers not fragrant. Fertile flowers single; sterile flowers double in form.

*Natural flowering season.*—Continuously flowering from June through September in Grand Haven, Mich.

*Flower longevity.*—Flowers last about two to three months on the plant.

*Quantity of flowers.*—Freely flowering; about seven sterile flowers and about 137 fertile flowers per terminal cluster.

*Inflorescence diameter.*—About 19 cm.

*Inflorescence height.*—About 6 cm.

*Flower diameter.*—Fertile flowers: About 4 mm. Sterile flowers: About 4.5 cm.

*Flower depth (height).*—Fertile flowers: About 6 mm. Sterile flowers: About 4.5 mm.

*Flower buds (fertile and sterile flowers).*—Length: About 3 mm. Diameter: About 2 mm. Shape: Obovate. Color: 146C.

*Petals (petals present only on fertile flowers; sterile flowers do not have petals).*—Quantity per flower: About four. Length: About 3 mm. Width: About 2 mm. Shape: Ovate. Apex: Acute. Base: Truncate. Margin: Entire. Texture, upper and lower surfaces: Smooth, glabrous. Color: When opening, upper surface: 66B. When opening, lower surface: 66C. Fully opened, upper and lower surfaces: 66C; color becoming closer to 184B with development.

*Sepals (present on both fertile and sterile flowers).*—Quantity per flower: Fertile flowers: About four. Sterile flowers: About ten. Length: Fertile flowers: About 2 mm. Sterile flowers: About 2 cm. Width: Fertile flowers: About 1 mm. Sterile flowers: About 1.7 cm. Shape: Fertile flowers: Linear. Sterile flowers: Ovate. Apex: Fertile flowers: Acute. Sterile flowers: Acute to obtuse. Base: Fertile flowers: Obtuse. Sterile flowers: Obtuse to attenuate. Margin, fertile and sterile flowers: Entire. Texture, fertile and sterile flowers, upper and lower surfaces: Smooth, glabrous. Color: Fertile flowers, when opening and fully opened, upper and lower surfaces: 143D. Sterile flowers: When opening, upper surface: 66B. When opening, lower surface: 66D. Fully opened, upper surface: 66D; color becoming closer to 66A with development. Fully opened, lower surface: 65A.

*Peduncles.*—Length: About 5 cm. Diameter: About 4 mm. Angle: About 30° from vertical. Strength: Strong. Texture: Smooth. Color: 189A.

*Pedicels.*—Length: Fertile flowers: About 6 mm. Sterile flowers: About 3.5 cm. Diameter: Fertile flowers: About 0.5 mm. Sterile flowers: About 1.5 mm. Angle: Fertile flowers: About 75° from vertical. Sterile flowers: About 90° from vertical. Strength, fertile and sterile flowers: Strong. Texture, fertile and sterile flowers: Smooth. Color: Fertile flowers: 64C. Sterile flowers: 65A.

*Reproductive organs (reproductive organs present only on fertile flowers; sterile flowers do not have reproductive organs).*—Stamens: Quantity per flower: About ten. Anther shape: Round. Anther length: About 0.5 mm. Anther color: 201D. Pollen amount: Moderate. Pollen color: 201D. Pistils: Pistil quantity per flower: About four. Pistil length: About 1 mm. Stigma shape: Elongate. Stigma color: 64A. Style length: Less than 1 mm. Style color: 64A. Ovary color: 64A. Seed: Seed development has not been observed.

Disease/pest resistance: Under commercial production conditions, plants of the new *Hydrangea* have not been observed to be resistant pathogens and pests common to *Hydrangea*.

Weather tolerance: Plants of the new *Hydrangea* have been shown to be tolerant to temperatures ranging from −25 to 34° C. Flowers of plants have exhibited excellent tolerance to wind and rain.

It is claimed:

1. A new and distinct cultivar of *Hydrangea* plant named 'Shamrock', as illustrated and described.

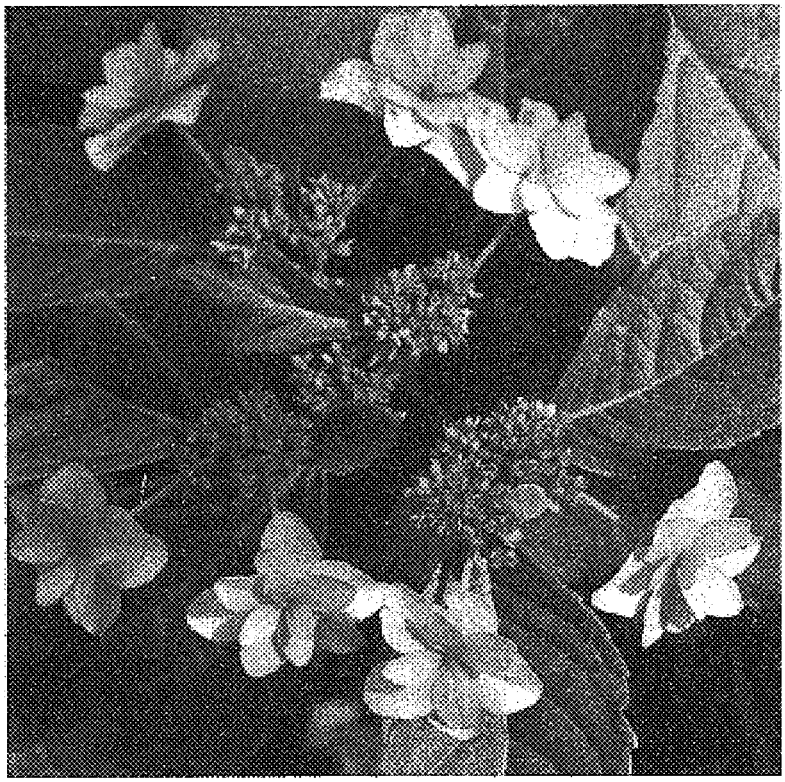
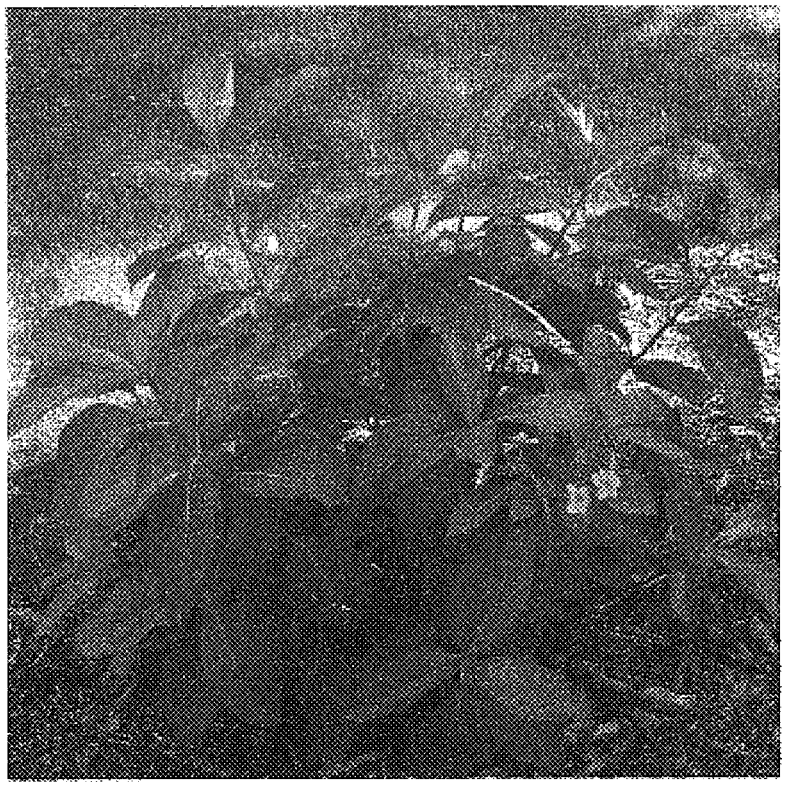

* * * * *